United States Patent
Bramlet et al.

(10) Patent No.: US 7,118,572 B2
(45) Date of Patent: Oct. 10, 2006

(54) FEMORAL NECK COMPRESSION SCREW SYSTEM WITH ORTHO-BIOLOGIC MATERIAL DELIVERY CAPABILITY

(75) Inventors: Dale G. Bramlet, St. Petersburg, FL (US); Peter M. Sterghos, St. Petersburg, FL (US)

(73) Assignee: Orthopedic Designs, Inc., St. Petersburg, FL (US)

( * ) Notice: Subject to any disclaimer, the term of this patent is extended or adjusted under 35 U.S.C. 154(b) by 0 days.

(21) Appl. No.: 10/766,666

(22) Filed: Jan. 27, 2004

(65) Prior Publication Data

US 2004/0193162 A1    Sep. 30, 2004

Related U.S. Application Data

(60) Provisional application No. 60/444,735, filed on Feb. 3, 2003.

(51) Int. Cl.
  *A61B 17/58*    (2006.01)
(52) U.S. Cl. .......................................... 606/66; 606/65
(58) Field of Classification Search ................ 606/73, 606/232
  See application file for complete search history.

(56) References Cited

U.S. PATENT DOCUMENTS

| | | | |
|---|---|---|---|
| 3,791,380 A | * | 2/1974 | Dawidowski ................ 606/68 |
| 4,653,489 A | | 3/1987 | Tronzo |
| 4,760,844 A | | 8/1988 | Kyle |
| 5,514,138 A | | 5/1996 | McCarthy |
| 5,849,004 A | | 12/1998 | Bramlet |
| 6,183,474 B1 | * | 2/2001 | Bramlet et al. ................ 606/65 |
| 6,443,954 B1 | | 9/2002 | Bramlet et al. |

* cited by examiner

*Primary Examiner*—Eduardo C. Robert
*Assistant Examiner*—Daniel Jacob Davis
(74) *Attorney, Agent, or Firm*—McHale & Slavin PA

(57) ABSTRACT

This device addresses the treatment of femoral neck trauma which includes basilar, mid-cervical and sub-cap fractures. The assembly has a lag screw assembly, side plate, compression screw and cortical screw, which are implantable. A syringe adaptor instrument delivers ortho-biologic material to the fracture site through the lag screw assembly. The lag screw assembly utilizes a cannulated screw with external threads and deployable tangs to anchor into the femoral head and is implanted in such a manner as to have the lag screw threads and tangs located on the opposite side of the fracture from the side plate. The distal shaft of the lag screw interfaces with the side plate in a manner which allows axial translation only. To deliver ortho-biologic material to the fracture site, the syringe adaptor instrument is inserted into the cannulated lag screw prior to the installation of the compression screw and the material is forced through it and out exit holes located circumferentially around the lag screw between the fracture site and the deployable tangs.

10 Claims, 6 Drawing Sheets

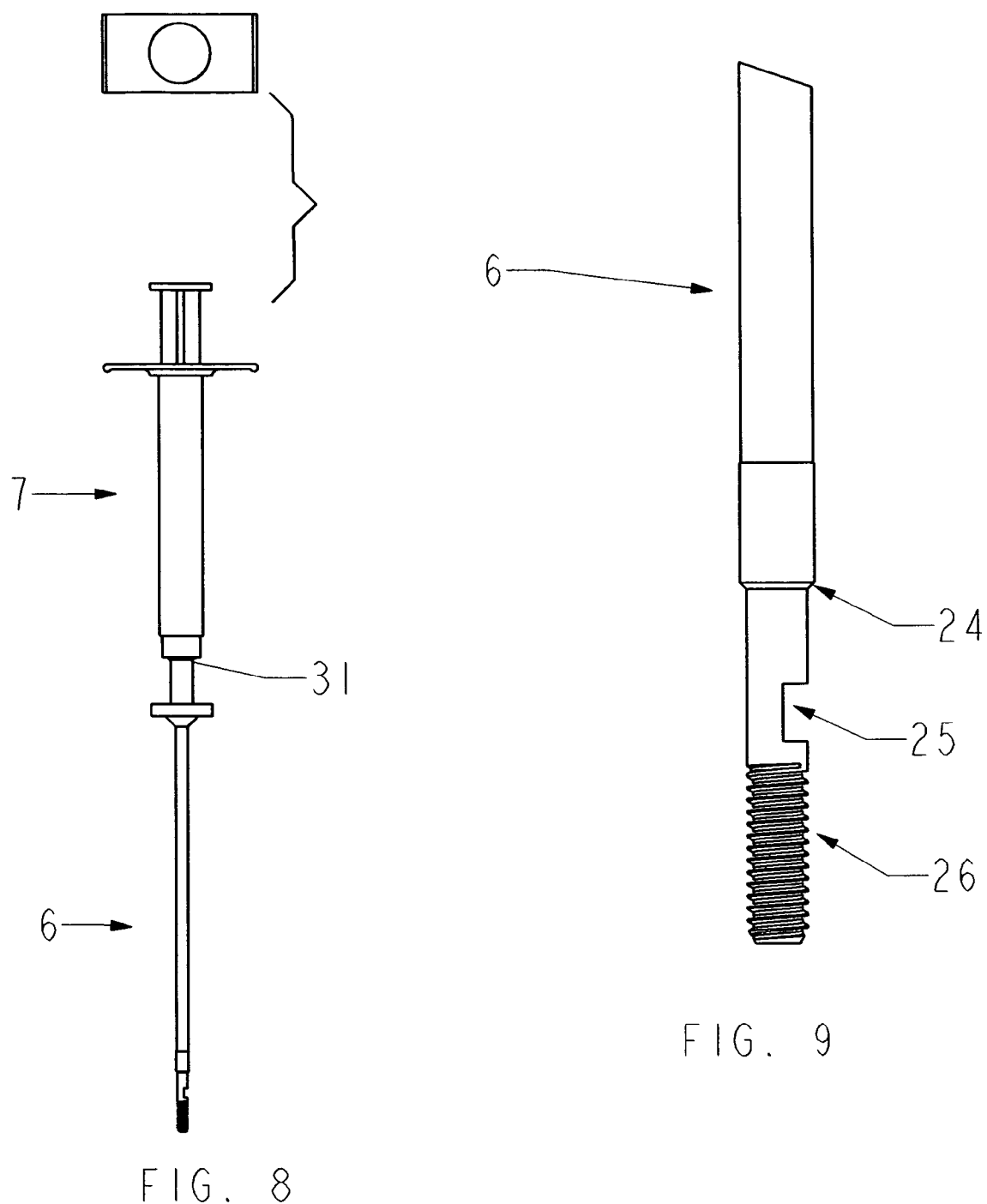

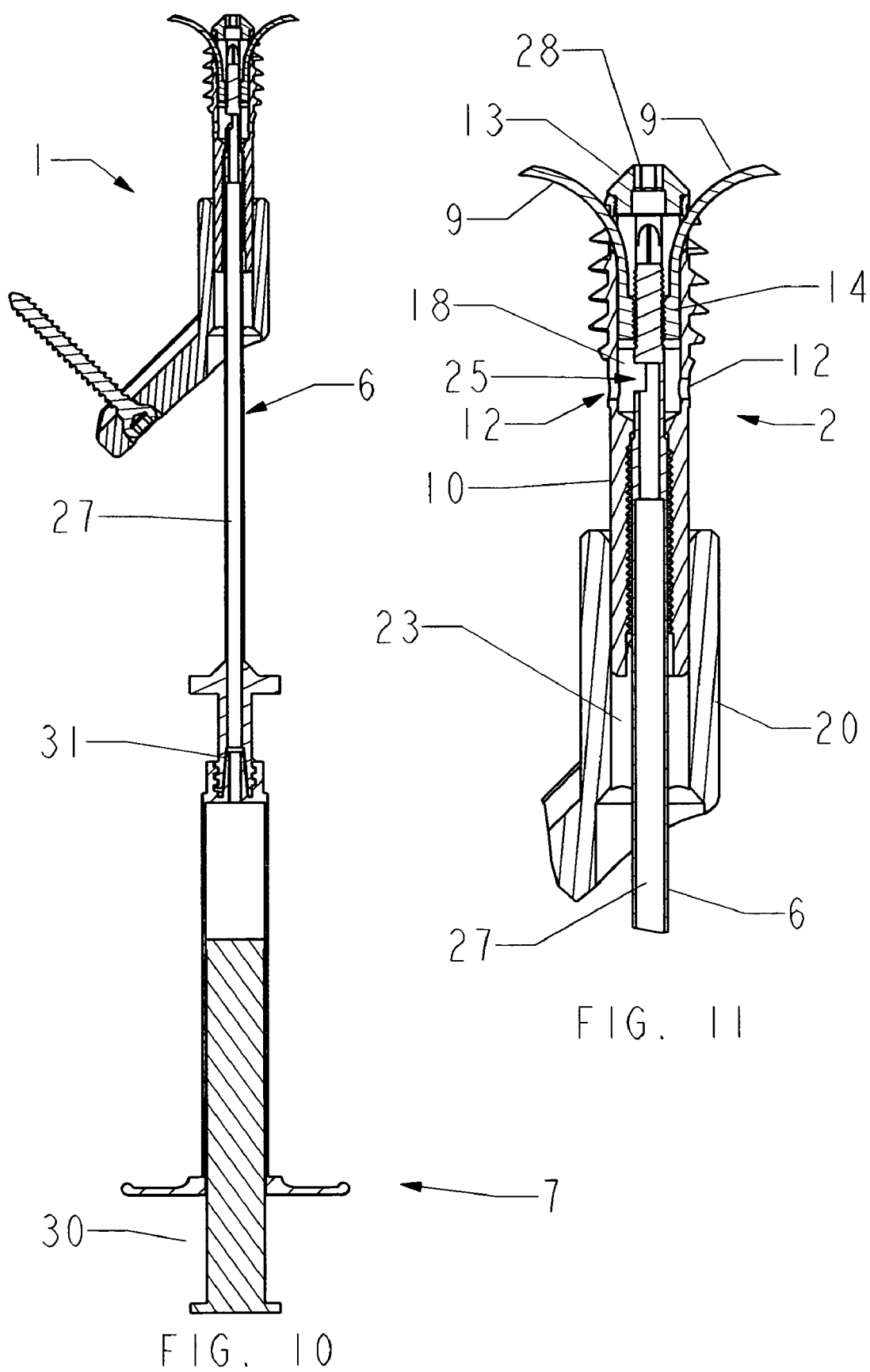

FEMORAL NECK COMPRESSION SCREW SYSTEM WITH ORTHO-BIOLOGIC MATERIAL DELIVERY CAPABILITY

RELATED APPLICATIONS

This application claims the benefit of the filing date of U.S. Provisional Application No. 60/444,735 filed Feb. 3, 2003 under 35 U.S.C. 119(e).

BACKGROUND OF THE INVENTION

1. Field of the Invention

This invention relates to the field of orthopedic surgery and, in particular, the treatment of fractures by implantation of bone screws for compression and medication.

2. Description of the Prior Art

The use of bone screws for stabilization and fixation of fractures is conventional. The use of lag screws for compression of fractures is also conventional, as shown by McCarthy, U.S. Pat. No. 5,514,138.

Lag screws and anchors with additional holding devices are taught by Bramlet, U.S. Pat. No. 5,849,004 and U.S. Pat. No. 6,443,954. These devices have curved talons which deploy from the interior of a cannulated body to increase the holding power.

Bone pins or screws have been used to access the interior of bones for application of diagnostic and structural components. For example, Kyle, U.S. Pat. No. 4,760,844, teaches the use of a cannulated screw for applying X-ray opaque dye and U.S. Pat. No. 4,653,489 teaches the use of a cannulated lag screw to apply polymethylmethacrylate (PMMA) or bone cement to the interior of a broken bone. In both these devices, the exuded material exits near the distal end of the screw which places the material in the immediate area of the screw threads.

What is lacking in the prior art is a lag screw with devices to increase the holding power of the screw and medicate the afflicted area while maintaining the ability to remove the devices and the screw.

SUMMARY OF THE PRESENT INVENTION

A device for the treatment of a femoral neck trauma which includes basilar, mid-cervical and sub-cap fractures. The device is a compression screw assembly having a side plate, a compression screw and a cortical screw, which are implantable. A syringe adaptor instrument delivers ortho-biologic material to the fracture site through the lag screw. The lag screw assembly utilizes a cannulated screw with external threads and deployable tangs to anchor into the femoral head and is implanted in such a manner as to have the lag screw threads and tangs located on the opposite side of the fracture from the side plate. The distal shaft of the lag screw interfaces with the side plate in a manner which allows axial translation only. To deliver ortho-biologic material to the fracture site, the syringe adaptor instrument is inserted into the cannulated lag screw prior to the installation of the compression screw and the material is forced through it and out exit holes located circumferentially around the lag screw between the fracture site and the deployable tangs.

Thus, an objective of this invention is to repair fractures with a compression screw assembly exerting compression across of the fragments of the bone.

Another objective is to inject a biological material through the compression screw assembly into the area of the fracture to aid in recovery.

A further objective of this invention is to provide the lag screw assembly with a separation between the screw threads and the injection ports.

Yet another objective of this invention is to provide the injection assembly with a seal between the injection ports and the screw threads.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 8 is a side view of the syringe and adapter;

FIG. 9 is a side view of the adapter showing the exit port;

FIG. 10 is a longitudinal cross section of the compression screw assembly with the syringe and syringe adapter in place; and FIG. 11 is a longitudinal cross section of the lag screw and adapter showing the deployment of the tangs and location of the material discharge hole with the exit port.

DETAILED DESCRIPTION OF THE INVENTION

Figures 1, 2:
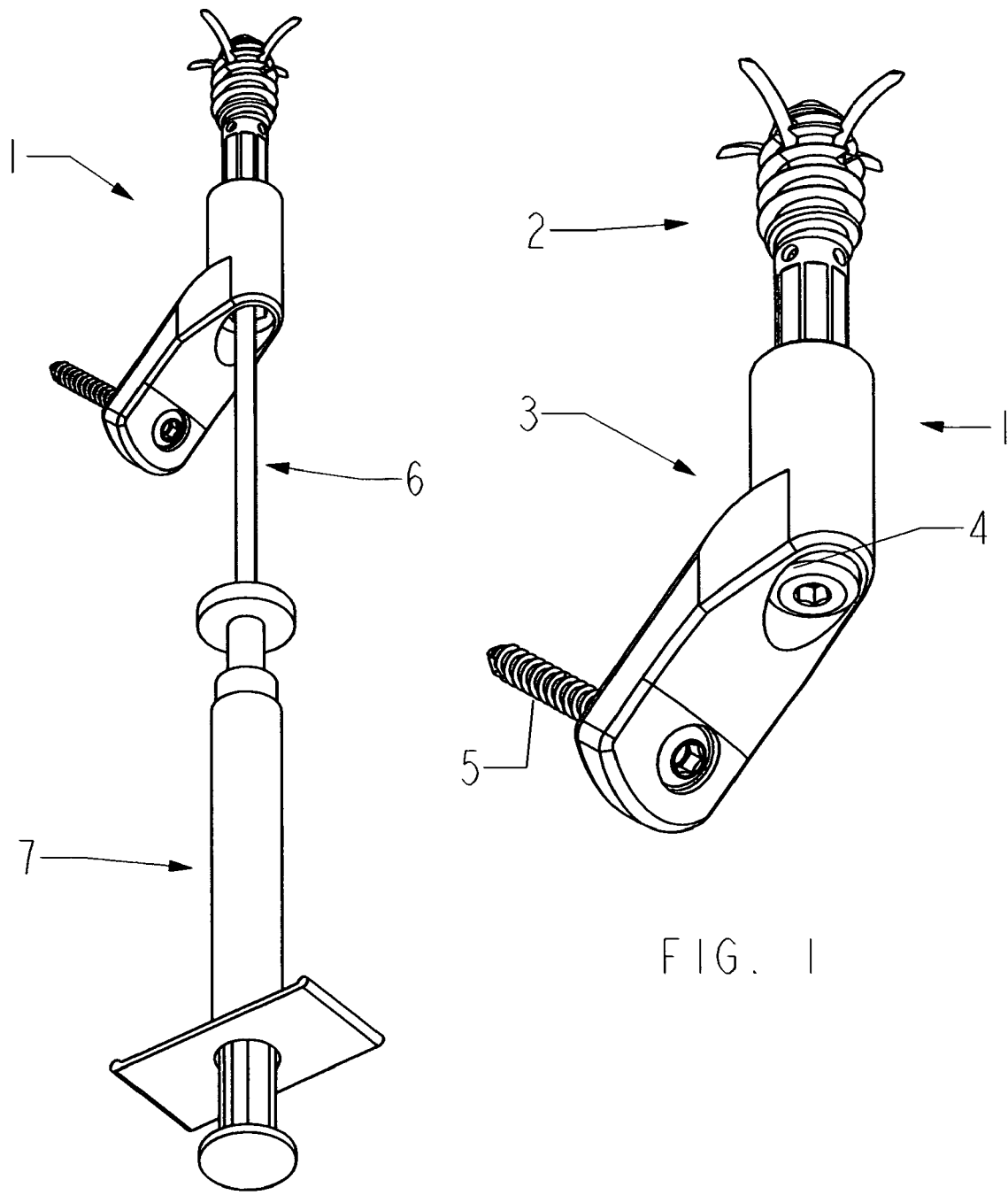
FIG. 1 is a perspective of the compression screw assembly.
FIG. 2 is a perspective of the compression screw assembly and the biological material syringe.
Figure 4:
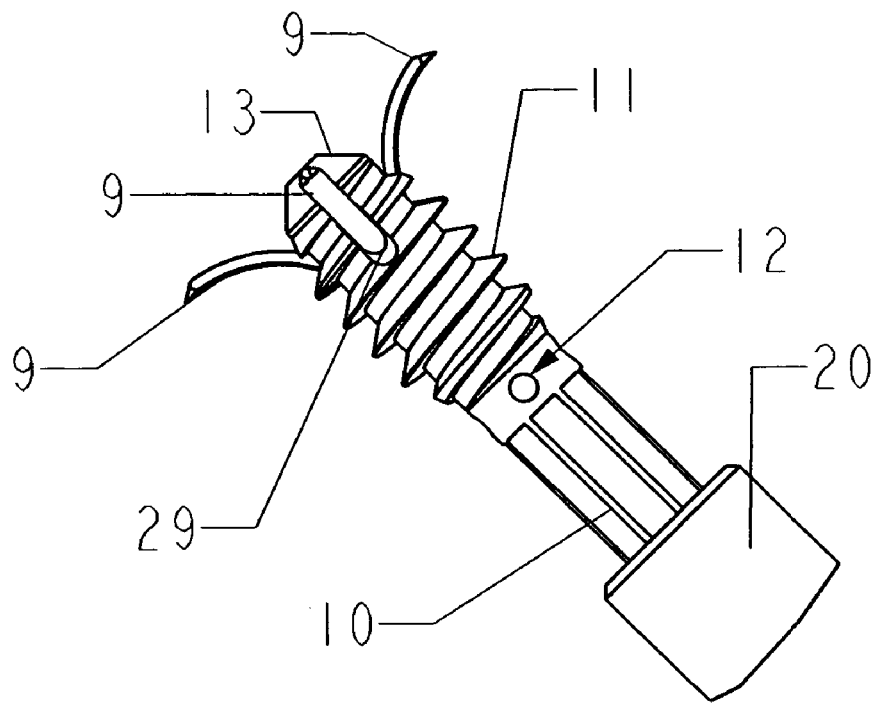
FIG. 4 is a side view of the lag screw showing extended tang legs.
Figure 3:
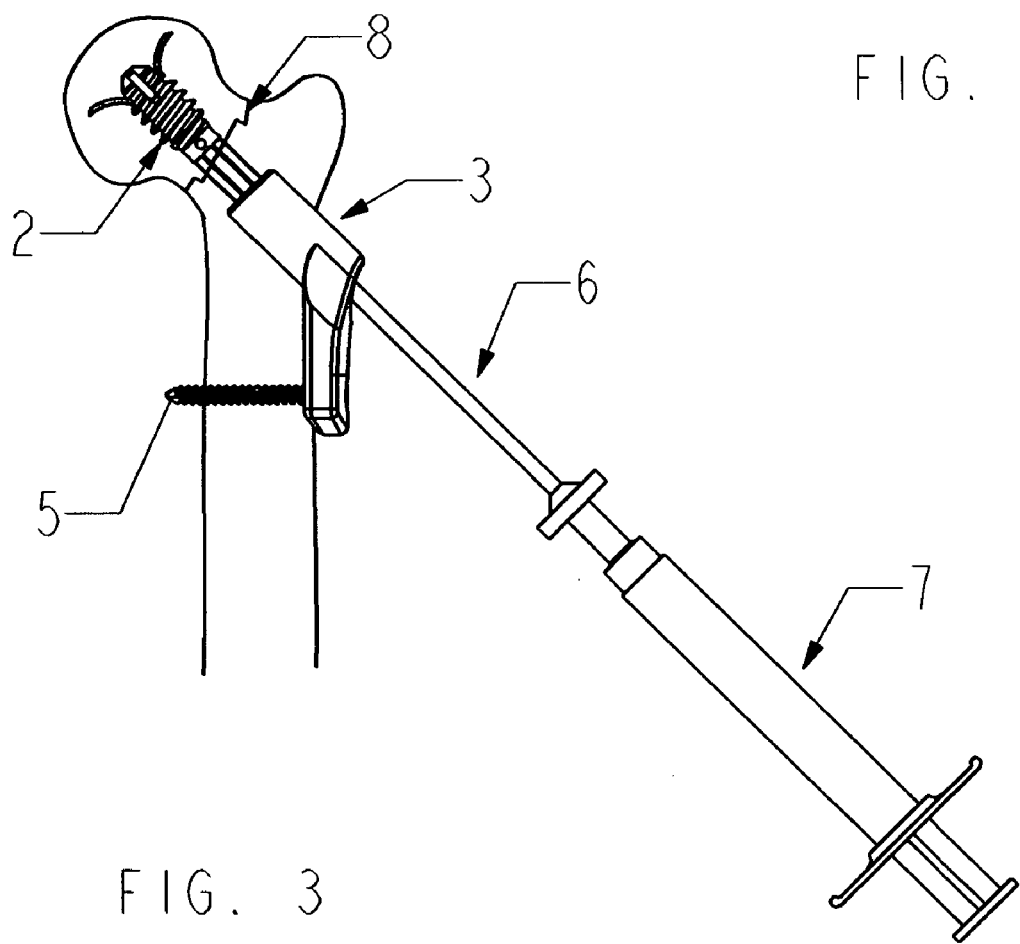
FIG. 3 is a perspective of the compression screw assembly and syringe in situ in a hip joint.

The implantable components 1, constructed of stainless steel or titanium alloy, or other medically acceptable materials shown in FIG. 1 include the lag screw assembly 2, side plate 3, compression screw 4 and cortical screw 5. FIG. 2 illustrates the implantable assembly 1, less compression screw 4, with syringe adaptor 6 and syringe 7 assembled to deliver ortho-biologic material to the fracture site 8, shown in FIG. 3 through the lag screw assembly 2. FIG. 3 also illustrates proper placement of the implant assembly with tang legs 9 and screw thread 11 located on the proximal side of fracture 8 and side plate 3 on the distal side of fracture 8 and ortho-biologic material discharge holes 12 in close proximity of the fracture 8.

Figures 5, 6:
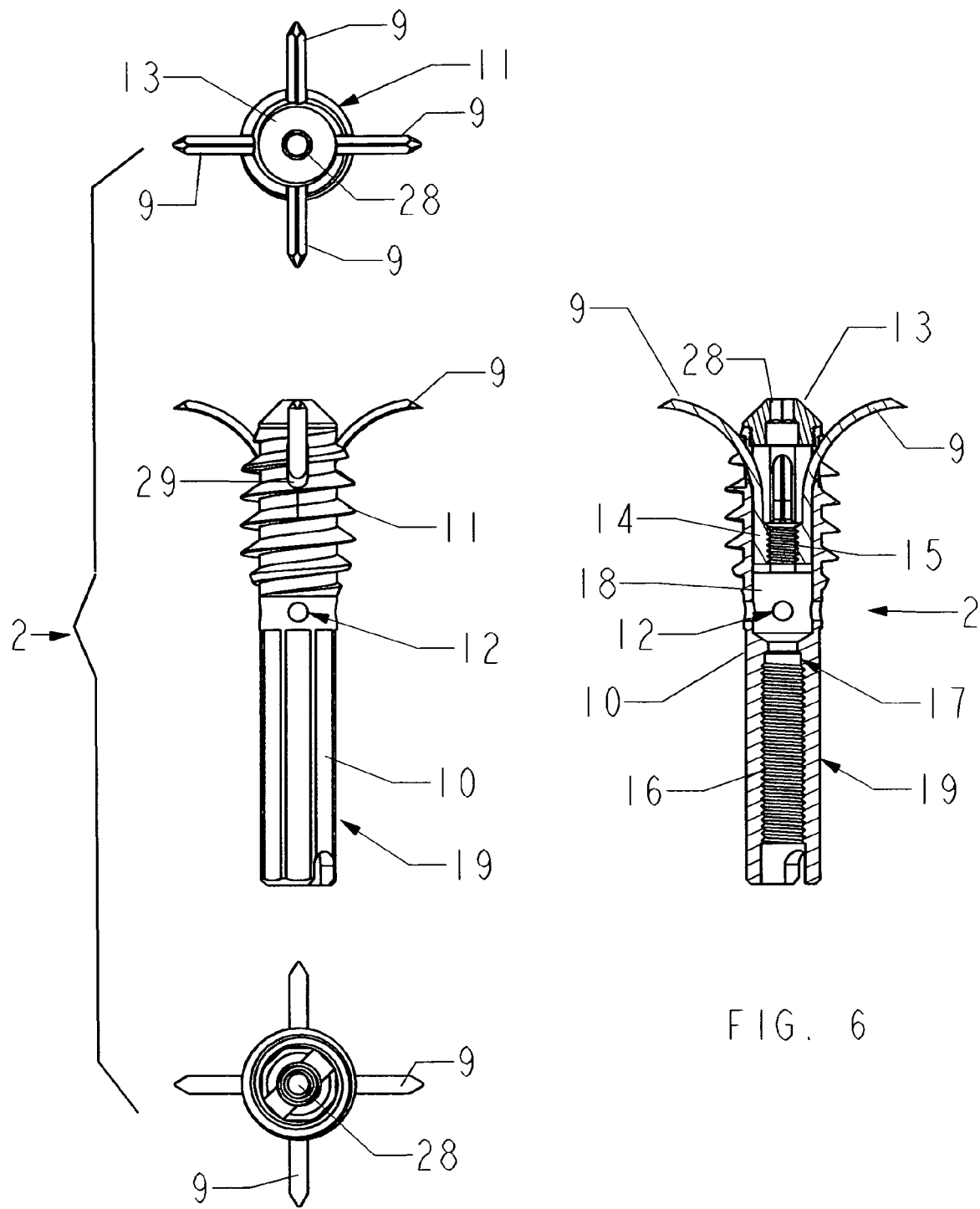
FIG. 5 is a composite a side view of the lag screw including an end view of the leading end and the trailing end of the lag screw.
FIG. 6 is a side view, partially in section, of the lag screw.

The lag screw assembly 2, as shown in FIGS. 5 and 6, contains two concentric bores, the tang clearance bore 28 and compression screw bore 16 which is threaded for engagement with compression screw 4. An end cap 13 is utilized to capture the tang body 14 within the clearance bore 18. The end cap 13 has a clearance bore through it to allow passage of a guide wire (not shown) during the installation of the lag screw assembly 2. Ortho-biologic material discharge holes 12 extend through the lag screw assembly 2 wall into the tang clearance bore 18. The tang body 14, shown in the deployed position, consists of a body with four integral tang legs 9 and a threaded bore 15. In its non-deployed position, the entire tang is contained within lag screw assembly tang bore 18. Deployment of tang 14 occurs when the tang 14 is translated toward the end cap 13 at which time tang legs 9 are forced out of tang exit holes 29. Tang threaded bore 15 provides clearance for a guide wire during lag screw assembly 2 installation and instrument interface for tang 14 retraction. The non-threaded portion 10 of lag screw body 19, in its preferred embodiment, has an octagonal cross section.

Figure 7:
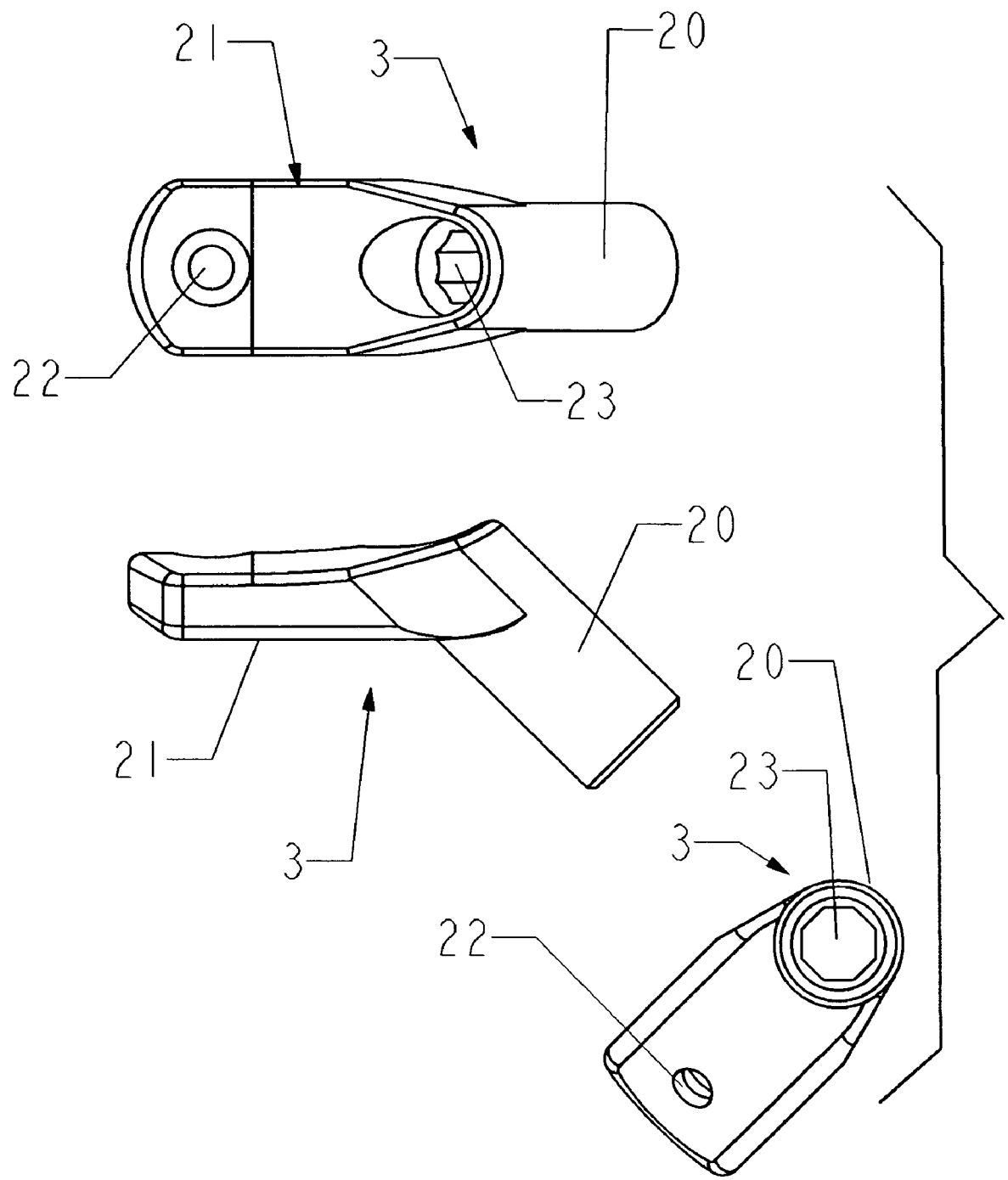
FIG. 7 is a composite of the side plate showing a side view a front view and a bore view.

The side plate 3, in FIG. 7, consists of a body 21 and barrel 20. The body 21 contains a through hole 22 for cortical screw 5 clearance. The barrel 20 contains octagonal bore 23 which is sized to allow insertion of the compression screw octagonal body portion 10 and a sliding fit thereby allowing only translation without rotation. The compression screw 4 inserts through side plate barrel 20 and threads into lag screw threaded bore 16 when the lag screw assembly octagonal body 10 is inserted into lag screw barrel octagonal barrel bore 23. As the compression screw 4 is advanced, the head of compression screw 4 contacts and reacts with side plate 3 and forces lag screw assembly 2 to translate distally. Since lag screw threads 11 and tang legs 9 are engaged into bone on the proximal side of the fracture 8 and the side plate 3 is located on the distal side of fracture 8, fracture 8 is reduced or compressed. Cortical screw 5 is threaded into bone through clearance hole 22 preventing translation or rotation of side plate 3 and since relative rotation is prevented as previously described between lag screw 2 and side plate 3 and the tang legs 9 are engaged in the bone of the femoral head, rotation of the femoral head and fracture is prevented.

The syringe adaptor 6, in FIG. 8, has a standard Leuer interface 31 at one end for connection to any standard syringe 7. At the opposite end of the syringe adaptor 6 is an external thread 26 a exit port 25 and a shoulder 24. An internal bore 27, shown in FIG. 11, runs the entire length of syringe adaptor 6 to the exit port 25 and intersects the exit port 25 but does not continue into the external thread 26. After implanting the implant assembly 1 less the compression screw 4 the syringe adaptor 6 is inserted through side plate barrel bore 23, through lag screw assembly compression screw bore 16, through lag screw assembly tang clearance bore 18. The external thread 26 of syringe adaptor 6 is then engaged into threaded bore 15 of tang body 14 and advanced until shoulder 24 of syringe adaptor 6 makes contact with lag screw assembly shoulder 17. At this point syringe 7 is attached to syringe adaptor 6 by means of the Leuer interface 31 of FIG. 10 or any other connector.

To introduce the ortho-biologic material, plunger 30 of syringe 7 is depressed forcing the material through the internal bore 27 of syringe adaptor 6 and out the syringe adaptor fluid exit port 25 into the lag screw assembly tang clearance bore 18. For example, the ortho-biologic material may be selected from such groups of substances as bone cements, such as PMMA and other adhesives, BMP, bone morphogenic proteins, DBM, demineralized bone matrix, BOTOX and other viral vectors, any bone marrow aspirate, platelet rich plasma, composite ceramic hydroxyapatite, tricalcium phosphate, glass resin mixtures, resorbable highly purified polylacttides/polylactides-co-glycolides and others. The treating agent may include hormonal, antibiotic, anti-cancer, or growth factor substances, among others.

With tang body 14 having a close fit in lag screw assembly tang clearance bore 18 and syringe adaptor external thread 26 engaged in tang body internal thread 15 and syringe adaptor shoulder 24 in contact with lag screw assembly shoulder 17, the fluid is forced to exit through lag screw assembly ortho-biologic material exit holes 12 and into the proximity of the fracture 8. After, the material is delivered, the syringe adaptor 6 is removed and compression screw 4 is engaged and the fracture 8 is compressed/reduced as previously described.

It will be understood that various modifications may be made without departing from the spirit and scope of the invention. Accordingly, it is to be understood that the invention is not to be limited by the specific illustrated embodiment but only by the scope of the appended claims.

We claim:

1. A compression screw assembly for delivery of an ortho-biological material to a fracture site comprising a lag screw, a side plate, an elongated adapter, and a compression screw, said lag screw having an elongated body with a leading end, a distal end, and a longitudinal bore, external threads on said leading end for engaging a bone proximal to a fracture site, said leading end of said lag screw having at least one tang exit hole, a tang body movably disposed in said longitudinal bore and having at least one tang leg mounted to a first end, said tang leg adapted to translate through said at least one tang exit hole upon movement of said tang body, and a second end of said tang body having internal screw threads adapted to seal said tang body, said distal end of said lag screw adapted to extend distally of said fracture site, a first connector on said distal end, at least one discharge hole in said elongated body between said external threads and said distal end, said side plate having a body with a distal surface and a proximal surface, an aperture in said plate sized to accommodated said distal end of said lag screw whereby said side plate is adapted to slide along said elongated body and exerts compressive force between an enlarged head and said external threads, said adapter being of a size to telescope within said through bore of said elongated body, said elongated adapter having a bore extending from one end and terminating in a fluid exit port near the other end, said other end beyond said fluid exit port having external screw threads adapted to engage said internal screw threads in said tang body, said one end adapted to be connected with a syringe and said fluid exit port adapted to register with said discharge hole in said elongated body whereby ortho-biological material may be delivered to a fracture site, said compression screw having said enlarged head on one end and a second connector on the other end, said second connector on said compression screw adapted to mate with said first connector whereby said compression screw exerts a compressive force between said enlarged head and said external threads reducing the fracture.

2. A compression screw assembly of claim 1 comprising said distal end of said elongated body shaped for non-rotational movement and said aperture shaped for sliding longitudinally along said body.

3. A compression screw assembly of claim 2 comprising a barrel on said proximal surface of said side plate surrounding said aperture.

4. A compression screw assembly of claim 1 comprising a barrel on said proximal surface of said side plate surrounding said aperture.

5. A compression screw assembly of claim 4 comprising a cortical screw hole in said side plate.

6. A compression screw assembly of claim 1 comprising a cortical screw hole in said side plate.

7. A compression screw assembly kit for delivery of an ortho-biological material to a fracture site comprising a lag screw, a compression screw, a side plate, and an adapter, said lag screw having external threads and at least one tang exit hole at one end adapted to fix said lag screw in a bone proximal to a fracture site, a bore extending from said one end to the other end, said bore having internal threads in said other end, a circumferential seal in said bore spaced distally from said external threads, a discharge hole in said bore between said external threads and said other end, said side plate having an aperture adapted to telescope with said other end of said lag screw, said adapter having one end, a connector on the other end and a bore from said connector terminating in a fluid exit port near said one end, said adapter having a circumferential shoulder between said fluid exit port and said connector, a movable tang body in said bore between said discharge hole and said external threads, said tang body having at least one tang lea on one end and a seal on the other end, said one end of said adapter sized to engage said seal on said tang body whereby upon insertion of said adapter into said lag screw said one end of said adapter engages said seal in said tang body and said tang body is moved within said bore to register said fluid exit port and said discharge hole thereby extending said tang leg from said tang exit hole, said compression screw having an enlarged head on one end and external threads on the other end, said connector sized to pass through said aperture of said side plate and engage said internal threads in said through bore of said lag screw, said head adapted to engage said body of said side plate, whereby said lag screw may be threadably fixed in a bone proximal to a fracture site, said adapter is insertable into said lag screw with said shoulder engagable with said seal and said fluid exit port registered with said discharge hole, said connector adapted to mate with a source of ortho-biological material for permitting said ortho-biological material to flow through said adapter and out the discharge hole in the vicinity of said fracture site, said adapter being removable, said side plate adapted to be telescoped with said lag screw and said compression screw being insertable through said aperture for threadable engagement with said internal threads to apply compressive force between said side plate and said lag screw to reduce said fracture.

8. A compression screw assembly kit of claim 7 comprising said seal in said tang body being threads, said one end of said adapter having threads whereby threadably engaging said adapter threads and said tang body threads forms a seal.

9. A compression screw assembly for reduction of a fracture comprising a lag screw, an adapter, and a compression screw, said lag screw having an elongated body with a leading end, a distal end, and a longitudinal bore, external threads on said leading end for engaging a bone proximal to a fracture site, a tang body movably mounted in said longitudinal bore, said tang body having at least one tang leg, at least one tang exit hole formed in said leading end communicating with said longitudinal bore, said adapter sized to telescope through said longitudinal bore and engage and move said tang body toward said leading end and said tang leg extends through said tang exit hole as said tang body is moved toward said leading end, said adapter having a bore extending from one end and terminating in a fluid exit port near the other end, said distal end of said lag screw adjustably connected to one end of a compression screw having an enlarged head on the other end, said compression screw adapted to adjust the interval between said external threads and said enlarged head whereby said compression screw exerts a compressive force between said enlarged head and said external threads reducing the fracture.

10. A compression screw assembly of claim 9 comprising an end cap mounted in said leading end of said longitudinal bore.

* * * * *